United States Patent [19]
Witkowski et al.

[11] 3,991,078

[45] Nov. 9, 1976

[54] N-SUBSTITUTED 1,2,4-TRIAZOLES

[75] Inventors: Joseph T. Witkowski, Laguna Niguel; Roland K. Robins, Santa Ana, both of Calif.

[73] Assignee: ICN Pharmaceuticals, Inc., Irvine, Calif.

[22] Filed: Mar. 18, 1974

[21] Appl. No.: 452,213

Related U.S. Application Data

[63] Continuation-in-part of Ser. No. 240,252, March 31, 1972, Pat. No. 3,798,209, which is a continuation-in-part of Ser. No. 149,017, June 1, 1971, abandoned.

[52] U.S. Cl. .......................... 260/308 R; 424/269; 536/23
[51] Int. Cl.² ............... C07D 249/10; C07D 405/04
[58] Field of Search ................................ 260/308 R

[56] References Cited
OTHER PUBLICATIONS

Suganama et al., Chem. Abstracts, vol. 79, Abstract No. 706r (1973).
Sidwell et al., Chem. Abstracts, vol. 77, Abstract No. 147645n (1972).

*Primary Examiner*—Alton D. Rollins
*Attorney, Agent, or Firm*—Thomas D. Kiley; Kay H. Boswell

[57] ABSTRACT

Antiviral 1-(G)-1,2,4-triazole carboxamides, thiocarboxamides and carboxamidines wherein G is an acid labile hydrocarbon moiety, e.g., 1-($\alpha$-alkoxyalkyl), are prepared by, e.g., the acid-catalyzed addition reaction of appropriately substituted 1,2,4-triazole and an $\alpha,\beta$-unsaturated ether.

14 Claims, No Drawings

N-SUBSTITUTED 1,2,4-TRIAZOLES

CROSS-REFERENCE TO RELATED APPLICATIONS

This is a continuation-in-part of our application Ser. No. 240,252, filed Mar. 31, 1972, now U.S. Pat. No. 3,798,209, which is in turn a continuation-in-part of our application Ser. No. 149,017, filed June 1, 1971 and now abandoned. The disclosure of these applications is expressly incorporated herein by reference.

BACKGROUND AND BRIEF SUMMARY OF THE INVENTION

As reported in our aforesaid U.S. patent applications, we have discovered that certain 3-substituted-1-($\beta$-D-ribofuranosyl)-1,2,4-triazoles, notably the 3-carboxamide, 3-thiocarboxamide and 3-carboxamidines, possess potent antiviral activity. Those applications detail the preparation of precursors of the bioactive 1,2,4-triazole nucleosides (and corresponding cyclic and non-cyclic phosphorylated analogs) by processes involving either reaction of trimethyl-silylated 1,2,4-triazoles with O-acyl halo sugars, or acid-catalyzed fusion of appropriately 3-substituted 1,2,4-triazole with tetra-O-acyl sugar. Aminolysis of resulting 1-($\beta$-D-ribofuranosyl)-1,2,4-triazole-3-alkyl carboxylates affords the bioactive 3-carboxamide, while similarly formed 3-cyano-1-($\beta$-D-ribofuranosyl)-1,2,4-triazoles may be converted in straight forward fashion to corresponding 3-thiocarboxamides and 3-carboxamidines, respectively by reaction with hydrogen sulfide or ammonia.

In the later of our aforesaid applications, and in our application Ser. No. 340,332 filed Mar. 12, 1973 now U.S. Pat. No. 3,927,216, we report discovery of the antiviral activity of the known compounds 1,2,4-triazole-3-carboximide, and 1,2,4-triazole-3-thiocarboxamide, and preparation of the corresponding 1-$\beta$-D-riboside by reaction of the former with the enzyme Nucleoside phosphorylase. These bioactive bases are but poorly soluble. We conceived that solubility and lipophilicity of the bioactive bases could be enhanced, and in the course of doing so have prepared a novel class of N-substituted 1,2,4-triazole analogs of the antiviral ribosides which, unlike the latter, are readily susceptible to hydrolytic cleavage under conditions encountered in vivo, generating the 3-substituted 1,2,4-triazole base in situ. Although we do not wish to be bound by any theory, we believe that base is then promoted enzymatically to corresponding 1($\beta$-D-ribofuranosyl)-1,2,4-triazole nucleosides and/or nucleotides enroute to formation of truly active metabolite. According to this invention, there are provided novel compounds of structure

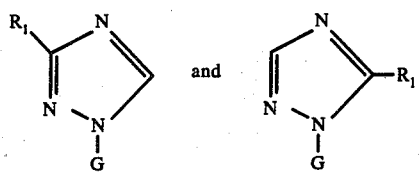

wherein $R_1$ is selected from the group consisting carboxamido, thiocarboxamido and carboxamidine groups and physiologically acceptably acid addition salts of the latter (in the case of bioactive compounds) or of cyano or alkylcarboxylate groups (in the case of intermediates useful in the synthesis of the former compounds). G in the foregoing structures is a hydrocarbon moiety (preferably linked through carbon to the triazole ring) chosen in one embodiment such that the bond G-N is activated toward hydrolysis to an extent sufficient to effect at least about 50% conversion to 3-$R_1$-1,2,4-triazole in about one hour at 37° C in "simulated gastric fluid" (as used herein, a pH 1.3 solution consisting of 2.0 gm. NaCl, 7.0 ml. concentrated HCl and sufficient water to make up 1000 ml. solu.), as determined by ultraviolet spectroscopy. As candidates for the group G may especially be mentioned groups in which an electronegative atom such as nitrogen or oxygen is alpha to that carbon linked directly to nitrogen of the triazole ring. As to the former, see the N-carbamoyl-1,2,4-triazoles of H. Becker and V. Eisenschmidt, *Journal f. prakt. Chemie* 315, 640 (1973) and W. German *Offen.* 2,147,794. As to the latter, see, e.g., the 1,2,4-triazole N-carbonic acid esters of "The Chemistry of 1,2,4-triazoles" by K. T. Potts, *Chem. Review* 61, 87, (1961). The aforesaid publications are incorporated herein by reference. Preferred in the practice of the invention are compounds in which G is a nonglycosidic 1-($\alpha$-alkoxyalkyl) moiety i.e., a moiety of structure

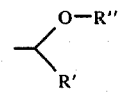

wherein R' and R'' are, e.g., aliphatic groups having 1 to about 9 carbon atoms or aliphatic groups joined to form a cyclic ether having 4 (tetrahydrofuran-2-yl) or 5(tetrahydropyran-2-yl) ring carbons. Since all the evidence in our hands supports the proposition that G is cleaved in vivo, it is unlikely that bioactivity can be made to depend upon nice choice of R' and R'', viz., they may bear physiologically acceptable substituents calculated not to interfere with hydrolytic scission of G following administration.

DESCRIPTION OF PREFERRED EMBODIMENTS OF THE INVENTION

Preferred embodiments of the invention may be obtained by the acid-catalyzed addition reaction of 1,2,4-triazole-3-$R_2$ (where $R_2$ is carboxamido, thiocarboxamido, cyano or alkylcarboxylate) with an $\alpha,\beta$-unsaturated ether, preferably in non-protic solvent media. Reaction occurs at less than about 100° C, preferably at temperature within the range from about 20 to about 80° C. Unduly high reaction temperature leads to competing polymerization of the unsaturated reactant, which is preferably employed in stoichiometric excess. In the resulting product G is the saturated analog of the

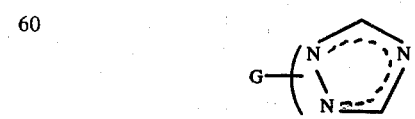

aforesaid ether. The N-substituted carboxamidine product may then be obtained from the 3- or 5-cyano compound just as in our aforesaid application Serial No. 240,252. Most preferably the $\alpha,\beta$-unsaturated ether is reacted with 3-cyano-1,2,4-triazole or 1,2,4-triazole alkyl carboxylate and the other 3-substituted compounds formed thereafter as in our application Ser. No. 240,252. Thus, 1-(G)-1,2,4-triazole-(3,5)-alkyl carboxylate undergoes aminolysis to the corresponding 3-carboxamide. Essentially any alkylcarboxylate may be employed, but for ease in byproduct separation, lower alkylcarboxylates (e.g., $C_1-C_4$, most preferably $C_1-C_2$) are recommended. Similarly, (3,5)-cyano-1-(G)-1,2,4-triazole is reacted with $H_2S$ in triethylamine or ammonia and ammonium chloride, ultimately respectively affording the compounds 1-(G)-1,2,4-triazole-(3,5)-thiocarboxamide and -(3,5)-carboxamidine.

EXAMPLE 1

1-(d,l-Tetrahydropyran-2-yl)-1,2,4-triazole-3-carboxamide

A mixture of methyl 1,2,4-triazole-3-carboxylate (12.7 g, 0.10 mole), 2,3-dihydropyran (16 ml), bis(p-nitrophenyl) phosphate (0.10 g) and anhydrous dimethylformamide (100 ml) was heated at 75°–80° for 3 hrs. Additional 2,3-dihydropyran (8 ml) was added and heating at 75°–80° was continued for 3 hrs. The solvent was removed in vacuo and the residue was dissolved in ethyl acetate (150 ml). The ethyl acetate solution was washed with aqueous sodium hydrogen carbonate (two 25 ml portions) and water. The solution was dried over magnesium sulfate, filtered and the filtrate was evaporated to dryness. The crude product, methyl 1-(d,l-tetrahydropyran-2-yl)-1,2,4-triazole-3-carboxylate, was treated for 20 hrs at 25° with methanol saturated with anhydrous ammonia. The solvent was removed in vacuo and the product was crystallized from ethanol to provide 14.0 g (71%). Recrystallization from ethanol afforded 11.7 g (60%) of pure 1-(d,l-tetrahydropyran-2-yl)-1,2,4-triazole-3-carboxamide with mp 156°–158°. NMR (DMSO-$d_6$) δ 8.82 (S, 1, H-5).

Anal. Calcd for $C_8H_{12}N_4O_2$: C, 48.97; H, 6.17; N, 28.56. Found: C, 48.95; H, 6.22; N, 28.42.

EXAMPLE 2

1-(d,l-Tetrahydrofuran-2-yl)-1,2,4-triazole-3-carboxamide

Methyl 1,2,4-triazole-3-carboxylate (6.35 g, 0.050 mole) was suspended in 75 ml of anhydrous dimethylformamide and bis(p-nitrophenylphosphate) (100 mg) was added. Then 2,3-dihydrofuran (7.0 g, 0.10 mole) was added dropwise at room temperature with stirring. The mixture was heated in a steel pressure bomb at 75° for 3.5 hr. The solvent was evaporated and the residue was dissolved in ethyl acetate. The solution was washed with aqueous sodium hydrogen carbonate and with water and was dried over magnesium sulfate (some of the product dissolved in the water and it was necessary to extract the aqueous solution with ethyl acetate). The organic solution was filtered and evaporated to dryness to give 9.1 g of a syrup. This syrup (9.0 g) was dissolved in methanol (150 ml) presaturated with ammonia at 0° and the solution was kept at room temperature overnight. The solvent was removed and the solid residue was co-evaporated several times with ethanol. The product was crystallized from ethanol to give 6.8 g (75%) of product. Recrystallization from ethanol provided 5.5 g (60%) of pure material with mp 171°–173°. NMR (DMSO-$d_6$) δ8.78 (S, 1, H-5).

Anal. Calcd for $C_7H_{10}N_4O_2$: C, 46.15; H, 5.52; N, 30.76. Found: C, 45.95; H, 5.51; N, 30.64.

EXAMPLES 3 AND 4

1-(1-Ethoxyethyl)-1,2,4-triazole-3-carboxamide and 1-(1-Ethoxyethyl)-1,2,4-triazole-5-carboxamide.

A mixture of methyl 1,2,4-triazole-3-carboxylate (25.4 g, 0.20 mole), dimethylformamide (200 ml), bis(p-nitrophenyl) phosphate (0.20 g), and ethyl vinyl ether (80 ml) was stirred in a stoppered flask at 25° for 120 hrs. The solvent was removed in vacuo and ethyl acetate (300 ml) was added to the residue. A small amount of insoluble material was removed by filtration and the filtrate was evaporated to a syrup. The crude product was treated at 25° for 24 hours with methanol saturated with anhydrous ammonia (300 ml). The solvent was removed in vacuo and addition of ethanol (100 ml) to the residue gave a crystalline product (12.0 g). Recrystallization from ethanol provided 10.0 g (27%) of pure 1-(1-ethoxyethyl)-1,2,4-triazole-3-carboxamide with mp 163°–166°.

NMR (DMSO-$d_6$) δ1.11 (t, 3, J=7Hz, $CH_3-CH_2-$), 1.70 (d, 3, J=6 Hz, $CH_3$), 3.44 (m, 2, $CH_3 CH_2-$) 5.80 (q, 1, J=6 Hz, C—H), 7.65 and 7.85 (2 S, 2, $NH_2$) 8.90 (s, 1, H-5).

Anal. Calcd for $C_7H_{12}N_4O_2$: C, 45.64; H, 6.57; N, 30.42. Found: C, 45.48; H, 6.61; N, 30.54.

The filtrate from crystallization of the above product was evaporated to dryness and the residue was extracted with hot ether (250 ml). The ether solution was filtered and the filtrate was evaporated to a small volume. Addition of cyclohexane gave a crystalline product 16.3 g (44%). Recrystallization from ether-cyclohexane provided pure 1-(1-ethoxyethyl)-1,2,4-triazole-5-carboxamide with mp 87°–89°.

NMR (DMSO-$d_6$) δ1.08 (t, 3, J=Hz, $CH_3-CH_2-$), 1.65 (d, 3, J=6 Hz, $CH_3-$), 3.35 (m, 2, $CH_3-CH_2-$), 6.76 (q, 1, J=6 Hz, C—H), 8.05 and 8.25 (2 S, 2, $NH_2$), 8.20 (s, 1, H-3).

Anal. Calcd for $C_7H_{12}N_4O_2$: C, 45.64; H, 6.57; N, 30.42. Found: C, 45.46; H, 6.47; N, 30.62.

EXAMPLE 5

3-Cyano-1-(d,l-tetrahydropyran-2-yl)-1,2,4-triazole

A solution of 3-cyano-1,2,4-triazole (4.70 g, 0.050 mole), 2,3-dihydropyran (5.0 ml) and bis(p-nitrophenyl)phosphate (0.10 g) in ethyl acetate (100 ml) was refluxed for 1.5 hr. The solution was cooled and washed with aqueous sodium hydrogen carbonate (two 25 ml portions) and water. The ethyl acetate solution was dried over magnesium sulfate, filtered and evaporated to dryness. Purification of the crude product by chromatography on a silica gel column with chloroform as eluant afforded pure 3-cyano-1-(d,l-tetrahydropyran-2-yl)-1,2,4-triazole (6.74 g, 76%) as an oil. This product was characterized by the nmr spectra ($CDCl_3$, δ8.43; DMSO-$d_6$, δ9.17) and by conversion to 1-(d,l-tetrahydropyran-2-yl)-1,2,4-triazole-3-thiocarboxamide as described below.

EXAMPLE 6

1-(d,l-Tetrahydropyran-2-yl)-1,2,4-triazole-3-thiocarboxamide

Method 1

A solution of 3-cyano-1-(d,l-tetrahydropyran-2-yl)-1,2,4-triazole (1.78 g, 0.010 mole) and triethyl amine (5.0 ml) in ethanol (50 ml) was stirred at room temperature while hydrogen sulfide gas was bubbled into the solution for 2 hr. The solvent was removed under reduced pressure and the product was crystallized from ethanol to afford the thiocarboxamide (2.10 g, 99%) with m.p. 157°–159°.

Method 2

A mixture of 1,2,4-triazole-3-thiocarboxamide (1.28 g, 0.010 mole), 2,3-dihydropyran (5.0 ml), bis(p-nitrophenyl) phosphate (50 ml) and dimethylformamide (50 ml) was stirred at room temperature for 48 hr. The resulting solution was evaporated to dryness and the residue was triturated with ethyl acetate (30 ml). The product was collected by filtration to afford 1.80 g (85%) of the thiocarboxamide. Recrystallization from ethanol afforded 1.40 g of pure product with m.p. 157°–159°.

Anal. Calcd for $C_8H_{12}N_4OS$: C, 45.26; H, 5.70; N, 26.40; S, 15.11. Found: C, 45.19; H, 5.80; N, 26.46; S, 15.23.

Compounds of the invention are tested for activity in vivo against influenza $A_2$ (Japan 305) induced deaths in male Swiss mice (18–21 gram), and the results compared to those obtained with compounds known to be active [1-($\beta$-D-ribofuranosyl)-1,2,4-triazole-3-carboxamide and 3-carbamoyl-1,2,4-triazole] and with analogous compounds demonstrably resistant to hydrolysis in simulated gastric fluid. The mice were intranasally inoculated with virus and treated with compound under test by oral administration twice daily for 9 days commencing 2 hours pre- and 4 hours post-virus inoculation. Infected mice were observed for 21 days. The results of testing are presented in Table I. All compounds tested were orally non-toxic at the doses employed.

TABLE I

EFFECTS OF COMPOUNDS ON INFLUENZA $A_2$ (JAPAN 305) - INDUCED DEATHS IN MICE

| No. | Compound Name | Virus Dose | Drug Dose (mg/kg/day) | Infected Survivors Total | Survivor Increase $P^a$ | Mean Survival Time (days) | Mean Survival Time Increase $P^b$ |
|---|---|---|---|---|---|---|---|
| — | Saline (control) | $2LD_{50}$ | 10 ml/kg/day | 1/40 | — | 7.7 | — |
| — | Saline (control) | $LD_{80}$ | " | 3/20 | — | 8.2 | — |
| 1. | 1-($\beta$-D-ribofuranosyl) 1,2,4-triazole-3-carboxamide | " | 75 | 6/10 | <0.05 | 9.3 | >0.05 |
| 2. | " | $2LD_{50}$ | 75 | 6/10 | 0.00008 | 9.3 | 0.05 |
| | | | 37.5 | 1/10 | >0.3 | 7.2 | — |
| 3. | 3-Carbamoyl-1,2,4-triazole | " | 300 | 5/10 | 0.0006 | 10.2 | <0.05 |
| | | | 150 | 4/10 | 0.004 | 9.3 | >0.05 |
| 4. | 1-(d,1-Tetrahydropyran-2-yl)-1,2,4-triazole-3-carboxamide | $3.2LD_{50}$ | 300 | 3/9 | >0.3 | 9.3 | <0.05 |
| | | | 150 | 2/9 | >0.3 | 7.6 | — |
| | | | 75 | 2/10 | >0.3 | 8.5 | >0.05 |
| | | | 37.5 | 1/10 | — | 5.6 | >0.05 |
| 5. | 1-(d,1-Tetrahydrofuran-2-yl)-1,2,4-triazole-3-carboxamide | $LD_{80}$ | 300 | 7/10 | <0.01 | 10.3 | >0.05 |
| | | | 150 | 0/10 | — | 8.7 | — |
| | | | 75 | 0/10 | — | 8.4 | — |
| | | | 37.5 | 0/9 | — | 6.9 | — |
| 6. | 1-(1-Ethoxyethyl)-1,2,4-triazole-5-carboxamide | $2LD_{50}$ | 300 | 7/10 | 0.000009 | 9 | — |
| | | | 150 | 6/10 | 0.00008 | 8.8 | >0.05 |
| | | | 75 | 5/10 | 0.0006 | 8.8 | >0.05 |
| | | | 37.5 | 1/10 | >0.3 | 7.4 | — |
| 7. | 1-(1-Ethoxyethyl)-1,2,4-triazole-3-carboxamide | " | 300 | 6/10 | 0.00008 | 9.3 | >0.05 |
| | | | 150 | 3/10 | 0.021 | 8.3 | >0.05 |
| | | | 75 | 1/10 | >0.03 | 7.8 | >0.05 |
| | | | 37.5 | 0.10 | — | 7.1 | |
| 8. | 1-($\beta$-D-ribofuranosyl)-1,2,4-triazole-5-carboxamide | " | 300 | 6/10 | >0.3 | 8.0 | >0.05 |
| | | | 150 | 2/10 | 0.092 | 7.4 | — |
| | | | 75 | 3/10 | 0.021 | 6.8 | — |
| | | | 37.5 | 1/10 | >0.3 | 7.3 | — |
| 9. | 1-(2'-deoxy-$\beta$-D-ribofuranosyl)-1,2,4-triazole-3-carboxamide | " | 300 | 0/10 | — | 8.3 | >0.05 |
| | | | 150 | 0/10 | — | 8.3 | >0.05 |
| | | | 75 | 2/9 | 0.078 | 8.7 | >0.05 |
| | | | 37.5 | 0/10 | — | 6.9 | — |
| 10. | 1-methyl-1,2,4-triazole-3-carboxamide | " | 300 | 1/10 | >0.3 | 7.1 | — |
| | | | 150 | 1/10 | >0.3 | 7.2 | — |
| | | | 75 | 1/10 | >0.3 | 7.1 | — |
| | | | 37.5 | 1/10 | >0.3 | 8.2 | >0.05 |

$^a$Probability (Chi Square Analysis)
$^b$Probability (t test)
$^c$Surviving animals were considered to have died on day 21

Various of the compounds tested in the above fashion were studied from the standpoint of hydrolysis in simulated gastric fluid at 37° C to 1,2,4-triazole-3-carboxamide as confirmed by thin-layer chromatography and infrared spectra. Per cent hydrolysis was determined by ultraviolet spectroscopy. Resulting data is reported in Table II.

TABLE II

| | Per Cent Hydrolysis in Simulated Gastric Fluid | | | | | | | |
|---|---|---|---|---|---|---|---|---|
| Compound No. | 5 Min | 20 Min | 40 Min | 60 Min | 2 Hr | 4 Hr | 6 Hr | 24 Hr |
| 1 | 0 | 0 | 0 | 0 | 0 | 0 | 0 | 0 |
| 4 | 10 | 44 | 69 | 85 | 96 | 97 | 98 | 100 |
| 6 | 100 | | | | | | | |

TABLE II-continued

| | Per Cent Hydrolysis in Simulated Gastric Fluid | | | | | | | |
|---|---|---|---|---|---|---|---|---|
| Compound No. | 5 Min | 20 Min | 40 Min | 60 Min | 2 Hr | 4 Hr | 6 Hr | 24 Hr |
| 7 | 11 | 44 | 71 | 81 | 98 | 100 | | |
| 8 | 0 | 0 | 0 | 0 | 0 | 0 | 10 | 60 |
| 9 | 0 | 0 | 0 | 2 | 10 | 28 | 50 | 100 |
| 10 | 0 | 0 | 0 | 0 | 0 | 0 | 0 | 0 |

Taken together, the foregoing experiments underline the apparent importance to activity of susceptibility to hydrolysis yielding base which, it is believed, is in turn ribosylated enroute to formation of the active metabolite.

Thus, each of active compounds 4, 6 and 7 were readily hydrolyzed to base in simulated gastric fluid, and each proved active in vivo. Compounds 8, 9 and 10 were neither readily hydrolyzed nor significantly active. Compounds 8, 9 and 10 were neither readily hydrolyzed nor significantly active. Compound (1, 2) of course, is active notwithstanding resistance to hydrolysis. In the case of this innately active compound cleavage to form base need not precede delivery of active metabolite to the source of infection.

The compounds of this invention may be administered generally as disclosed in our aforesaid application Ser. No. 340,332, the disclosure of which is incorporated herein by reference.

We claim:
1. An N-substituted 1,2,4-triazole of the structure

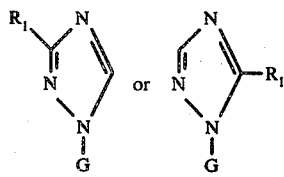

wherein $R_1$ is selected from the group consisting of carboxamido, thiocarboxamido, cyano, carboxamidino and its physiologically acceptable acid-addition salts and alkyl carboxylate groups and wherein G is a moiety of the structure

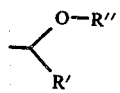

wherein R' and R'' are alkyl groups having from 1 to 9 carbon atoms or R' and R'', taken together, are trimethylene or tetramethylene.

2. A compound 1-(G)-1,2,4-triazole-3-$R_1$ according to claim 1.
3. A compound 1-(G)-1,2,4-triazole-5-$R_1$ according to claim 1.
4. A compound according to claim 2 wherein G is selected from the group consisting of tetrahydropyran-2-yl and tetrahydrofuran-2-yl groups.

5. A compound according to claim 3 wherein G is selected from the group consisting of tetrahydropyran-2-yl and tetrahydrofuran-2-yl groups.
6. A compound according to claim 1 wherein $R_1$ is carboxamido.
7. A compound according to claim 2 wherein $R_1$ is carboxamido.
8. A compound according to claim 3 wherein $R_1$ is carboxamido.
9. 1-(Tetrahydropyran-2-yl)-1,2,4-triazole-3-carboxamide.
10. 1-(Tetrahydrofuran-2-yl)-1,2,4-triazole-3-carboxamide.
11. 1-(1-Ethoxyethyl)-1,2,4-triazole-3-carboxamide.
12. 1-(1-Ethoxyethyl)-1,2,4-triazole-5-carboxamide.
13. 1-(Tetrahydropyran-2-yl)-1,2,4-triazole-3-thiocarboxamide.
14. A method of forming acid labile N-substituted 1,2,4-triazoles which comprises effecting the acid-catalyzed addition reaction, under anhydrous conditions, of 1,2,4-triazole of formula

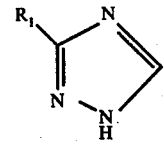

wherein $R_1$ is a cyano, carboxamido, thiocarboxamido or alkylcarboxylate group with an $\alpha,\beta$-unsaturated ether of the formula

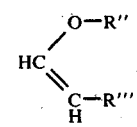

wherein R'' is alkyl of 1 to 9 carbons, inclusive, and R''' is hydrogen or alkyl of 1 to 8 carbon atoms, inclusive, or R'' and R''', taken together, are dimethylene or trimethylene to form compounds of structure

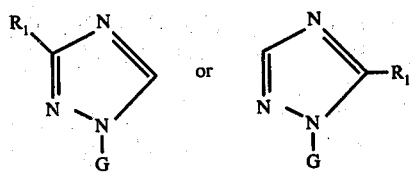

wherein G is as defined in claim 1.

* * * * *